(12) United States Patent
Berg et al.

(10) Patent No.: US 6,273,880 B1
(45) Date of Patent: Aug. 14, 2001

(54) CATHETERS WITH INTEGRATED LUMEN AND METHODS OF THEIR MANUFACTURE AND USE

(75) Inventors: Todd Allen Berg, Lino Lakes; Paul J. Hindrichs, Plymouth; Christopher Michael Prigge, New Hope, all of MN (US)

(73) Assignee: St. Jude Medical Anastomotic Technology Group, Inc., Maple Grove, MN (US)

( * ) Notice: Subject to any disclaimer, the term of this patent is extended or adjusted under 35 U.S.C. 154(b) by 0 days.

(21) Appl. No.: 09/375,915

(22) Filed: Aug. 17, 1999

Related U.S. Application Data (62) Division of application No. 09/010,367, filed on Jan. 21, 1998, now Pat. No. 6,013,190.

(51) Int. Cl.[7] .................................................. A61M 25/00
(52) U.S. Cl. ............................................. 604/523; 606/113
(58) Field of Search .................................. 606/108, 194, 606/114, 127, 128, 159, 191–193, 195–200, 205–208, 110, 113; 604/96–104, 19, 22, 264, 280, 265

(56) References Cited

U.S. PATENT DOCUMENTS

| | | | |
|---|---|---|---|
| 4,335,723 | * 6/1982 | Patel | 128/349 |
| 4,592,754 | 6/1986 | Gupta et al. | 623/1 |
| 4,638,667 | 1/1987 | Zimmer et al. | 73/432.1 |
| 4,739,768 | 4/1988 | Engelson | 128/658 |
| 4,748,984 | 6/1988 | Patel | 128/658 |
| 4,754,752 | * 7/1988 | Ginsburg et al. | 128/303.12 |
| 4,817,601 | 4/1989 | Roth et al. | 128/303.1 |
| 4,850,351 | 7/1989 | Herman et al. | 128/303.1 |
| 4,969,890 | 11/1990 | Sugita et al. | 606/192 |
| 5,125,895 | 6/1992 | Buchbinder et al. | 604/95 |
| 5,167,686 | 12/1992 | Wong | 65/4.21 |
| 5,254,107 | 10/1993 | Soltesz | 604/282 |

(List continued on next page.)

FOREIGN PATENT DOCUMENTS

| | | | |
|---|---|---|---|
| 2 313 899 | 9/1974 | (DE) | A61M/25/00 |
| 0 535 874 | 4/1993 | (EP) | A61M/25/00 |
| 664312 | 1/1952 | (GB) | . |
| WO 96/18361 | 6/1996 | (WO) | A61F/2/06 |
| WO 97/44082 | 11/1997 | (WO) | A61M/25/00 |
| WO 97/48434 | 12/1997 | (WO) | A61M/25/00 |

OTHER PUBLICATIONS

"Pebax® Resins, 33 Series Property Comparison," Technical Information, ATO Atochem Product Brochure, ATO Atochem (Dec., 1990).

"Fuouropolymer Heat Shrink Tubing," Zeus Product Brochure.

*Primary Examiner*—Richard K. Seidel
*Assistant Examiner*—Jennifer Maynard
(74) *Attorney, Agent, or Firm*—Fish & Neave; Robert R. Jackson; Laura A. Sheridan (57) ABSTRACT

A catheter with at least one integrated lumen and methods of its manufacture and use are provided. A method of manufacture includes: (1) covering a primary mandrel with a first layer, (2) disposing a second layer on the first layer, wherein the second layer has at least one removable secondary mandrel substantially embedded therein, (3) fusing the first layer to the second layer, (4) removing the secondary mandrel from the second layer to form a secondary lumen, and (5) removing the primary mandrel from the first layer to form a primary lumen. The method may further include forming an inflatable balloon at the surface of the second layer where the secondary lumen forms an opening. Also, auxiliary apparatus, such as snare instruments and bundles of optical fibers, may be inserted through the secondary lumen before or during use of the catheter.

11 Claims, 4 Drawing Sheets

U.S. PATENT DOCUMENTS

| | | | |
|---|---|---|---|
| 5,269,757 | 12/1993 | Fagan et al. | 604/95 |
| 5,279,596 | 1/1994 | Castaneda et al. | 604/282 |
| 5,287,861 | 2/1994 | Wilk | 128/898 |
| 5,297,564 | 3/1994 | Love | 128/898 |
| 5,342,299 | 8/1994 | Snoke et al. | 604/95 |
| 5,383,852 | 1/1995 | Stevens-Wright | 604/95 |
| 5,423,311 | 6/1995 | Snoke et al. | 128/6 |
| 5,437,288 | 8/1995 | Schwartz et al. | 128/772 |
| 5,460,610 * | 10/1995 | Don Michael | 604/101 |
| 5,522,834 | 6/1996 | Fonger et al. | 606/194 |
| 5,662,622 | 9/1997 | Gore et al. | 604/282 |
| 5,792,124 * | 8/1998 | Horrigan et al. | 604/282 |
| 5,843,116 * | 12/1998 | Crocker et al. | 606/192 |
| 5,911,725 * | 6/1999 | Boury | 606/108 |
| 6,068,603 * | 5/2000 | Suzuki | 600/565 |

\* cited by examiner

CATHETERS WITH INTEGRATED LUMEN AND METHODS OF THEIR MANUFACTURE AND USE

This application is a Div of Ser. No. 09/010,367 filed Jan. 21, 1998, now U.S. Pat. No. 6,013,190.

BACKGROUND OF THE INVENTION

This invention relates to medical devices and procedures used during the repair, replacement, or supplement of a medical patient's natural body organ structures or tissues. In particular, this invention relates to catheters with at least one integrated lumen for use in connection with such medical procedures and to methods of their manufacture.

Revascularization of the human heart is a good example of a medical procedure that involves the repair and supplement of a patient's body organ. Early procedures were known for revascularizing the human heart, but there were several disadvantages to these procedures. The earliest procedures involved exposing the heart by means of a midline sternotomy and stopping the beating of the heart to facilitate performance of the procedure. A graft is used to create a new, uninterrupted channel between a blood source, such as the aorta, and the occluded coronary artery or arteries downstream from the arterial occlusion or occlusions. Such a procedure has significant disadvantages, however, because it is highly invasive and requires general anesthesia. In fact, these disadvantages preclude the use of sternotomy procedures on many patients.

Less invasive procedures were later developed for revascularizing the heart, but these have disadvantages as well. For example, a thoracostomy involves surgical creation of ports in the patient's chest to obtain access to the thoracic cavity. Specially designed instruments are then inserted through the ports. Thoracostomy bypass procedures are less traumatic than sternotomy bypass procedures, but they are still too traumatic for some patients and may be inadequate when the number of surgical bypasses is large. Another procedure, which is known as a thoracotomy, revascularizes the human heart by gaining access to the thoracic cavity with incisions between the patient's ribs, but this procedure may still be too traumatic for some patients.

Goldsteen et al. U.S. patent application Ser. No. 08/745,618, filed Nov. 7, 1996, which is hereby incorporated by reference herein, discloses a less traumatic surgical technique for revascularizing the human heart. A key aspect of that invention involves the use of catheters that are inserted into a patient's body through relatively remote entry ports, such as a femoral (leg) artery of the patient, a brachial artery of the patient, or any other suitable entry point. Control of these instruments throughout their use is from a proximal portion that is outside the patient at all times. In order to minimize the number of entry ports or to perform any of the specialized surgical techniques disclosed therein, a single catheter instrument may include two or more lumens. However, as the number of lumens increases, conventional manufacturing methods may yield catheters that have outer diameters that are undesirably large, which may irritate sensitive vessels and preclude their use in narrow vessels. Furthermore, such catheters may be difficult to position and secure in a patient's body.

In view of the foregoing, it is an object of this invention to provide less traumatic methods and apparatus for revascularizing a patient.

It is another object of the invention to provide methods of manufacturing catheters with integrated lumens without substantially increasing the thickness of catheter walls.

It is still another object of the invention to provide a catheter that can create a hemodynamic seal when positioned across vessel walls.

It is yet another object of the invention to provide a catheter that can be positioned in a vessel and used to selectively secure one or more medical devices therein.

SUMMARY OF THE INVENTION

These and other objects of the invention are accomplished in accordance with the principles of the invention by providing a catheter having at least one secondary lumen. The catheter includes a first flexible tubular layer with a primary lumen or passageway inside, and a second flexible layer that is at least partially fused to the outer surface of the first layer. The second layer has at least one secondary lumen that is substantially integrated into the second layer and opens through the second layer at a secondary lumen opening. In a preferred embodiment according to this invention, the catheter may further include a structural layer that is located substantially between the first and second layers.

A method for making a catheter in accordance with this invention is also provided. In a first step, a primary mandrel is covered with a first layer having an outer surface. In a second step, a second layer is disposed on a portion of the outer surface of the first layer. The second layer substantially forms the catheter wall and has at least one removable secondary mandrel substantially embedded therein. In a third step, the first layer is fused to the second layer. In a fourth step, the secondary mandrels are removed from the second layer to form respective secondary lumens. Each of the secondary lumens opens at a surface of the second layer at a respective secondary lumen opening. A secondary lumen may extend through the first layer if the secondary opening is at the radially inner surface of the second layer. And in a fifth step, the primary mandrel is removed from the first layer to form a primary lumen.

Further features of the invention, its nature and various advantages will be more apparent from the accompanying drawings and the following detailed description of the preferred embodiments.

DETAILED DESCRIPTION OF THE PREFERRED EMBODIMENTS

According to the present invention, a catheter having at least one integrated lumen in a catheter wall, and methods for the manufacture and use of such a catheter, are provided. The method of manufacture involves covering a primary mandrel with a first layer and fusing a second layer, having at least one integrated lumen, to the outer surface of the first inner layer. The integrated lumen may be used to position or secure medical devices or to deliver fluids to a particular location anywhere along the catheter's length.

Figure 1A:
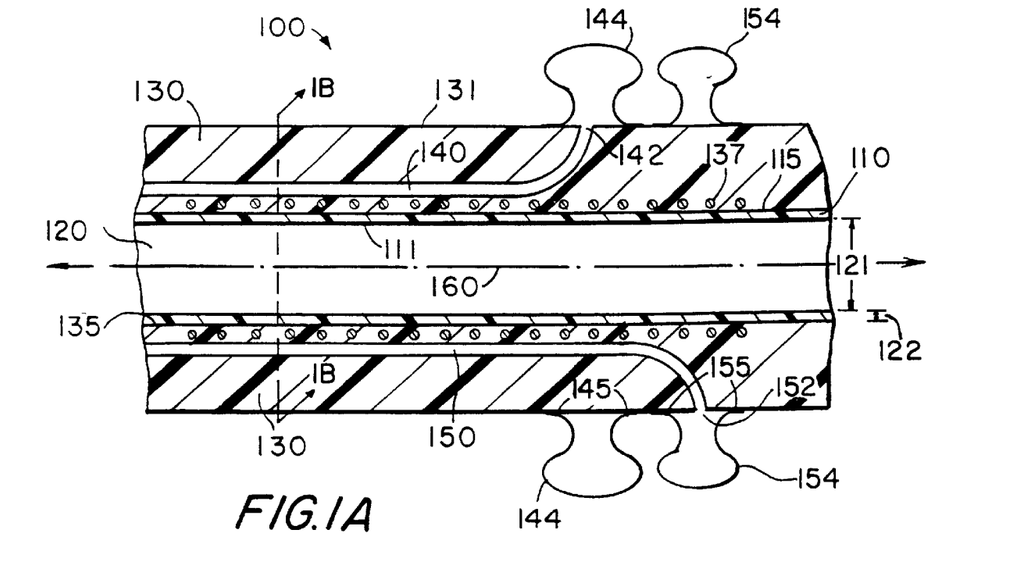
FIG. 1A is a longitudinal sectional view of an illustrative catheter with two integrated lumens in accordance with this invention.

As shown in FIG. 1A, catheter 100 includes at least first flexible layer 110 and second flexible layer 130 around longitudinal axis 160. First layer 110 has outer surface 115 and primary lumen 120, which extends longitudinally inside first layer 110. Second layer 130 has inner surface 135 that is at least partially fused to outer surface 115 of first layer 110. Second layer 130 has secondary lumens 140 and 150 that are substantially integrated into second layer 130 and open through second layer 130 at respective secondary lumen openings 142 and 152. As will be discussed more fully below, catheter 100 may further include structural layer 137, such as a metal braid or coil, which is substantially located between first layer 110 and second layer 130 for providing some rigidity to catheter 100.

Figure 1B:
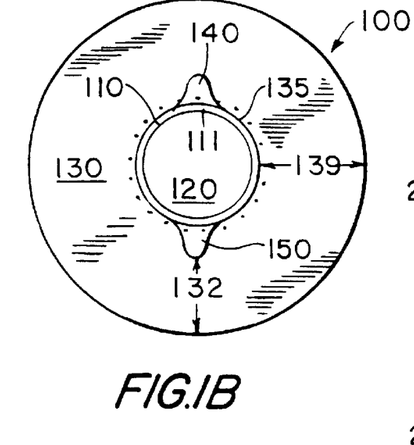
FIG. 1B is a cross sectional view of the illustrative catheter shown in FIG. 1A taken along line 1B—1B.

As shown in FIG. 1B, first layer 110 preferably has an elliptical cross section, most preferably a substantially cylindrical cross section. First layer 110 can be made from any flexible material, such as polymers. Polymers that may be used to make first layer 110 according to this invention include polytetrafluoroethylene (such as that sold under the trademark TEFLON® by E.I. du Pont de Nemours & Company, of Wilmington, Del.), polyetheramide (such as that sold under the trademark PEBAX®, by Ato Chemie, of Courbeboie, France), polyamide, or polyimide.

The magnitude of inner diameter 121 of first layer 110 depends on the particular vascular intervention for which catheter 100 is used, but can certainly range from about 0.050 inches to about 0.225 inches. First layer 110 is preferably thin and has a wall thickness 122 of between about 0.001 inches and about 0.003 inches. Second layer 130 may be any polymer that is capable of flowing when subject to elevated temperatures during fusing, such as polyetheramide, polyamide, or polyimide. Outer surface 115 of first layer 110 is preferably roughened to improve adhesion to inner surface 135 of second layer 130. Outer surface 115 may be roughened mechanically or chemically, but any roughening technique may be used. One type of chemical etching technique involves exposing the surface to tetrafluoroethylene (such as that sold under the trademark TETRA-ETCH®, by W.L. Gore & Associates, Inc., of Newark, Del.).

The second layer has at least one substantially integrated secondary lumen. As shown in FIG. 1A, second layer 130 has integrated secondary lumens 140 and 150. According to this invention, any number of secondary lumens could be integrated at nearly any location in second layer 130, depending on the particular vascular intervention. For example, two secondary lumens 140 and 150 provide fluid communication to inflatable balloons 144 and 154 that can form a hemodynamic seal at a vessel wall.

The locations of integrated lumens also depend on the particular vascular intervention. As best shown in FIG. 1B, catheter 100 has two secondary lumens 140 and 150 that are preferably substantially adjacent to inner surface 135 of second layer 130 and located on opposite sides of primary lumen 120. Secondary lumens 140 and 150 are preferably integrated near inner surface 135 to improve the strength of, and prevent kinking in, catheter 100. This inner surface arrangement is in contrast to an intermediate arrangement, where the secondary lumen is located intermediately between inner surface 135 and outer surface 131. That intermediate arrangement divides the wall thickness into two thinner portions which are not as structurally robust as the inner surface arrangement shown in FIGS. 1A and 1B. As shown in FIG. 1A, secondary lumens 140 and 150 also extend substantially parallel to longitudinal axis 160 for at least a portion of catheter 100.

Figure 2A:
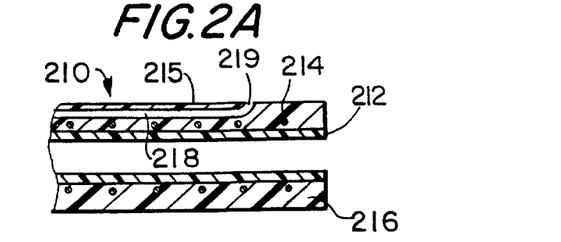
FIG. 2A is a simplified longitudinal sectional view showing a possible alternative construction of a secondary lumen in a catheter in accordance with this invention.
Figure 2B:
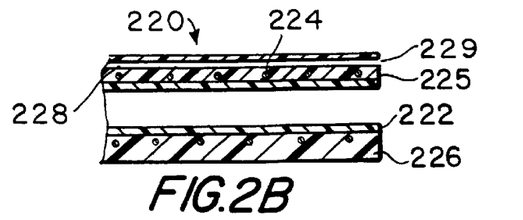
FIG. 2B is a simplified longitudinal sectional view showing another possible alternative construction of a secondary lumen in a catheter in accordance with this invention.
Figure 2C:
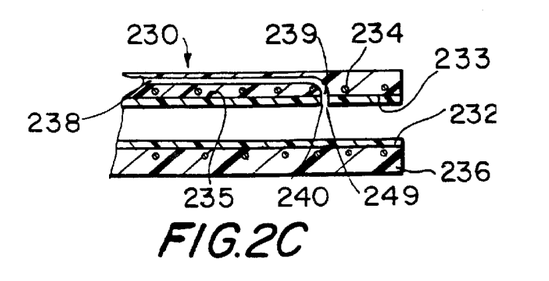
FIG. 2C is a simplified longitudinal sectional view showing yet another possible alternative construction of a secondary lumen in a catheter in accordance with this invention.

Although both ends of a secondary lumen are open to provide access to the secondary lumen, only the distal end of a secondary lumen is shown in the FIGS. That distal opening may be formed at any surface of the second layer. For example, FIGS. 2A–2C show catheters having secondary lumen openings on the radial outer surface, distal end, and radial inner surface of a second layer, respectively. In FIG. 2A, catheter 210 has first layer 212, structural layer 214, and second layer 216. Second layer 216 of catheter 210 has one secondary lumen 218, which has outer secondary lumen opening 219 at outer surface 215 of second layer 216. In FIG. 2B, catheter 220 has first layer 222, structural layer 224, and second layer 226. Second layer 226 of catheter 220 has one secondary lumen 228, which has distal secondary lumen opening 229 at distal end 225 of second layer 226. Finally, in FIG. 2C, catheter 230 has first layer 232, structural layer 234, and second layer 236. In catheter 230, second layer 236 has one secondary lumen 238, which has inner secondary lumen opening 239 at inner surface 235 of second layer 236. Catheter 230 also preferably has secondary lumen extension 240, which extends through first layer 232. Extension 240 extends from secondary lumen opening 239 to extension opening 249 located on inner surface 233 of first layer 232. In order to provide fluid communication between secondary lumen 238 and extension 240, structural layer 234, which acts like a flexible skeleton, is preferably porous. Structural layer 234, for example, may be made from any relatively stiff structural material, such as stainless steel braid or coil.

As shown in FIG. 1, catheter 100 may further include one or more inflatable balloons 144 and 154. These balloons are formed at respective secondary lumen openings 142 and 152 by covering the openings with elastic sheets or tubes, preferably bonded to outer surface 131 of second layer 130. Balloons 144 and 154 may also be formed from a single elastic sheet that covers both openings. In that case, a continuous strip of the sheet may be bonded to outer surface 131 of second layer 130 between openings 142 and 152 to form two separate compartments that are separately inflatable and deflatable. On the other hand, the balloons may be in fluid communication with each other so that only one secondary lumen is required to inflate or deflate, but the balloons in this case would not be independently controllable. Fluid communication between the balloons can be obtained by only partially bonding the strip of the sheet between the balloons. When two balloons are formed adjacent each other for gripping a vascular wall, as shown in FIGS. 1A and 3C, proximal secondary lumen opening 142 and distal secondary lumen opening 152 preferably have an axial separation that is greater than a thickness of the vascular wall. Because secondary lumens 140 and 150 extend outside of a patient during catheter use, the fluid pressure in the balloons can be monitored at the proximal end of the secondary lumen and controlled as desired.

The elastic sheets used to form balloons 154 and 154 may be bonded to outer surface 131 of second layer 130 by adhesive or heat treatment. The elastic sheet or tube may be made from any flexible material, such as polyurethane, silicone, rubber, and preferably latex materials (such as that products sold by The Pioneer Rubber Company, of Willard, Ohio or by California Latex Inc., of Pomona, Calif.). Preferably, the modulus of the elastic sheet or tube is between about 200 and about 2,500 psi. The outer surface of the balloon may be provided with channels to facilitate fluid flow when the balloon is inflated in a vessel. When the sheet has an annular shape that fits circumferentially around second layer 130, the sheet may be bonded to outer surface 131 along the sheet edges or tube ends to form an annular balloon. The elastic sheet or tube may be preformed before being bonded to outer surface 131 so that the sheet forms a hollow ring that opens radially inward. Preferably, the radially outer portion of the ring is larger than the radially inner portion of the ring so that a cross-section of the ring has a bulbous shape.

FIG. 3C shows catheter 370 (which is similar to catheter 100) secured to vascular wall 380 with a hemodynamic seal. Securing is preferably accomplished by at least partially inflating proximal balloon 374, inserting distal end 371 of catheter 370 through vascular wall 380 until wall 380 presses against inflated proximal balloon 374, and inflating distal balloon 372. Inflation of distal balloon 372 secures vascular wall 380 between balloons 372 and 374 and forms a hemodynamic seal between wall 380 and balloons 372 and 374. Although preinflation of proximal balloon 374 may be preferable to avoid over-insertion of catheter 370, both balloons may be deflated during the inserting step and inflated after the inserting step.

In addition to providing fluid communication to balloons, the secondary lumens may be used to position or secure the catheter itself or other auxiliary medical apparatus, or to deliver fluids to a particular location along the catheter's length.

Figure 3A:
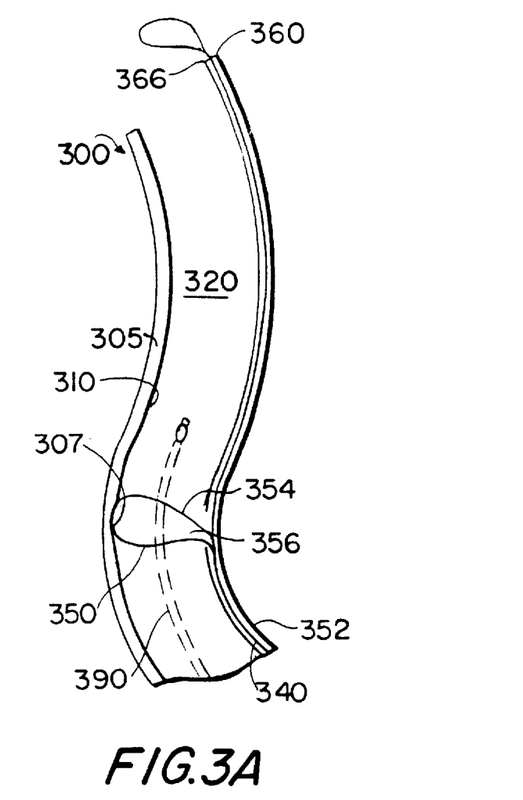
FIG. 3A is a simplified longitudinal sectional view showing a portion of an illustrative procedure using a snare instrument and related apparatus in accordance with the invention.

One such medical apparatus is endoscopic snare instrument 350 (see FIG. 3A). Instrument 350 includes shaft 352 with snare loop 354 at its distal end. Loop 354 is substantially closed when it is inside a snare sheath (not shown) or secondary lumen 340. Loop 354 may open resiliently to the shape shown in FIG. 3A when extended distally through secondary lumen opening 356 or when extended distally through secondary lumen opening 366 beyond distal end 360 of a sheath or secondary lumen 340.

Figure 3B:
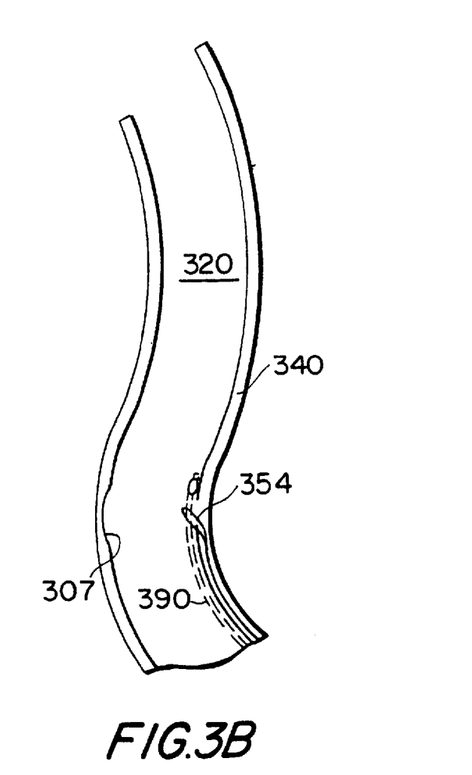
FIG. 3B is a simplified view similar to FIG. 2 showing a later stage in the illustrative procedure depicted in part by FIG. 3A, together with related apparatus, all in accordance with this invention.
Figure 3C:
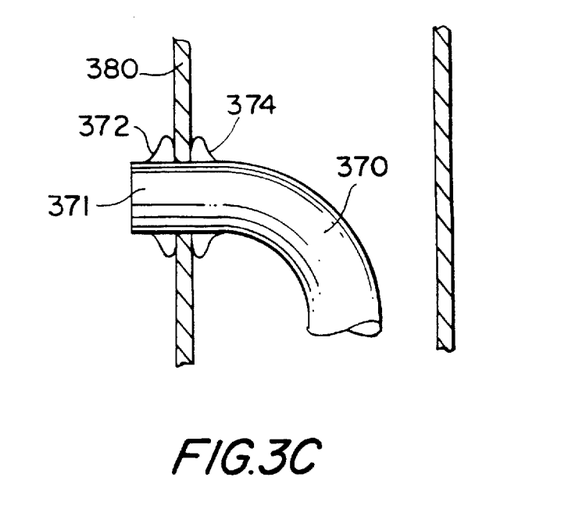
FIG. 3C is a simplified view showing the catheter of FIG. 1A passing through, and creating a hemodynamic seal at a vessel wall.

During operation, snare loop 354 may initially be in an open position in primary lumen 320 for subsequent securing of device 390 within primary lumen 320. In this case, inner surface 310 of catheter wall 305 may have recessed portion 307 for receiving open snare loop 354 so that loop 354 does not catch on device 390 when it is inserted through primary lumen 320. Once device 390 is inserted, loop 354 may be retracted into secondary lumen 340, as shown in FIG. 3B. In that case, snare loop 354 contracts and secures any guide wire, safety wire, or any other medial device 390 inside loop 354. As shown in FIG. 3A, a snare may be also be positioned at distal end 360 of catheter 300 for holding, snaring, or retrieving.

An advantage of using a snare instrument in a secondary lumen is that the principal catheter function (such as the installation of a new length of graft in a patient) and the secondary snare function (such as the securing of a device) may be performed simultaneously, eliminating the need to exchange one catheter for another during an operation.

The secondary lumen may guide, in addition to snare instruments, other auxiliary apparatus. For example, a secondary lumen may guide a fiber optic bundle for transmitting light to the vascular site or for transmitting an image of the vascular site to the doctor performing the operation. A single bundle of fibers may also perform both functions.

As described above, catheter 100 may include structural layer 137, such as a metal braid or coil. Structural layer 137 is located substantially between first layer 110 and second layer 130 for providing mechanical rigidity to catheter 100. As explained more fully below, the manufacture of catheter 100 involves fusing first layer 110 to second layer 130. In order to ensure proper bonding, structural layer 137 must not completely separate first layer 110 and second layer 130. Therefore, any porous structure that provides contact between first layer 110 and second layer 130, such as metal braid or coil, would be an appropriate structural material. Structural layer 137 may also be embedded directly in second layer 130 before bonding first layer 110 to second layer 130.

Figure 4:
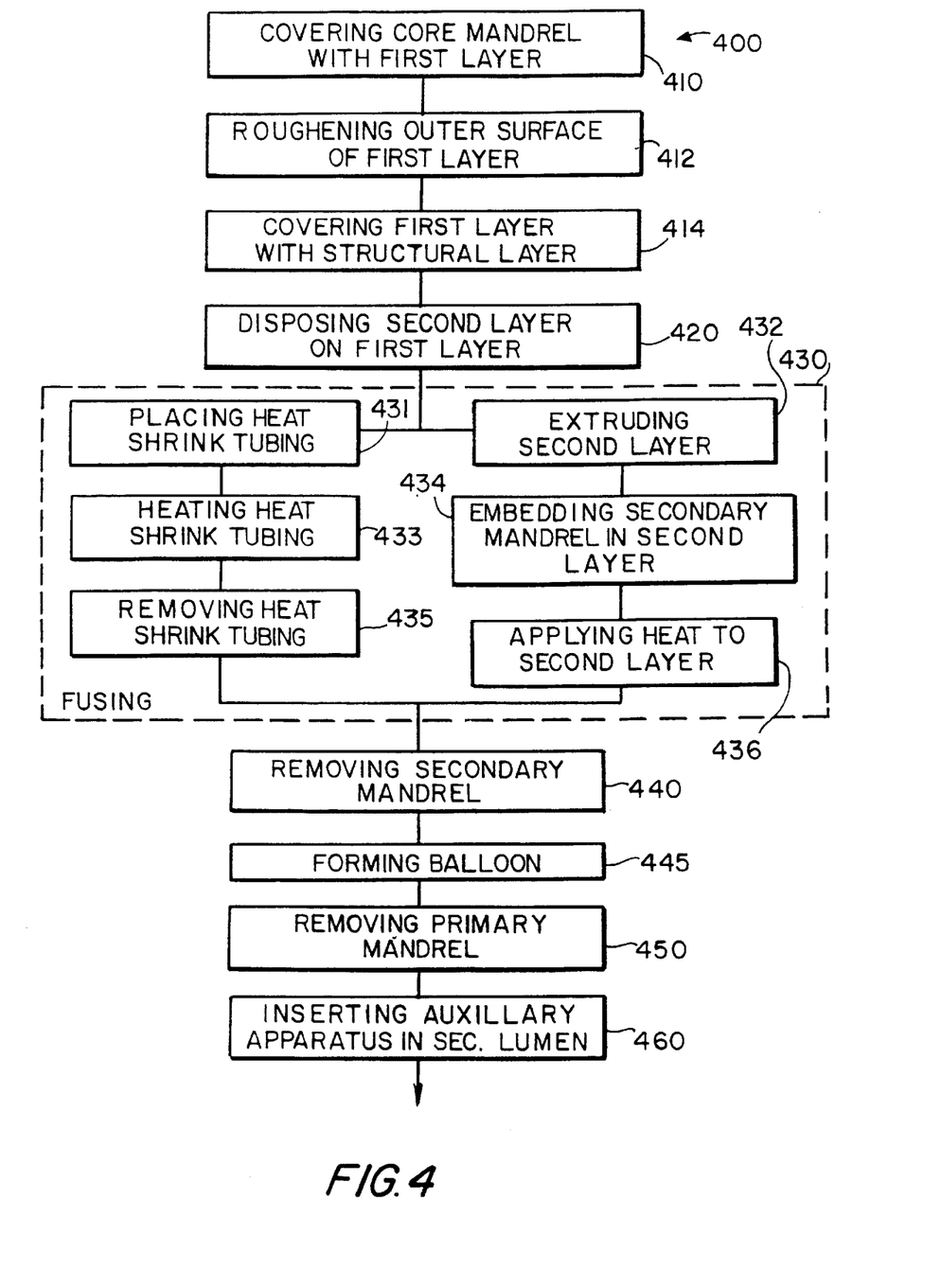
FIG. 4 is a flow chart of steps for carrying out an illustrative embodiment of the procedure for manufacturing a catheter having at least one integrated lumen according to this invention.

FIG. 4 shows an illustrative sequence of steps in accordance with this invention for manufacturing a catheter with at least one integrated lumen, such as catheter 100 shown in FIG. 1. These steps are described below with reference to FIGS. 5A–5F, which show catheter 100 at various intermediate manufacturing steps. To some extent these steps have already been mentioned, so the discussion of them here may be somewhat abbreviated.

A method in accordance with this invention for making a catheter with integrated lumens involves covering a primary mandrel with a first layer and fusing a second layer, which has at least one integrated lumen, to the outer surface of the first layer. The exact number and location of the secondary lumens is a matter of design.

Figure 5A:
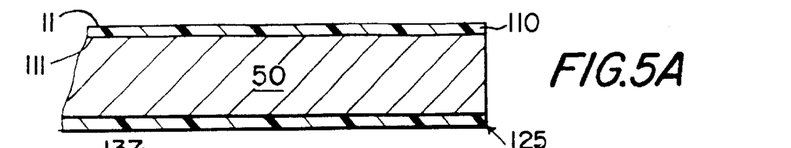
FIG. 5A is a longitudinal sectional view showing an initial stage in the FIG. 4 procedure.
Figure 5B:
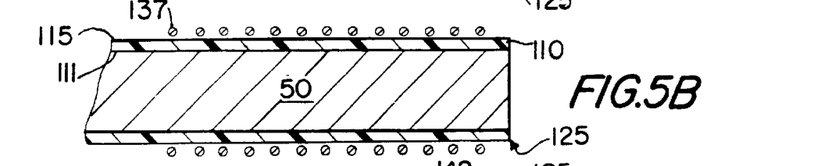
FIG. 5B is a view similar to FIG. 5A showing a later stage in the FIG. 4 procedure.
Figure 5C:
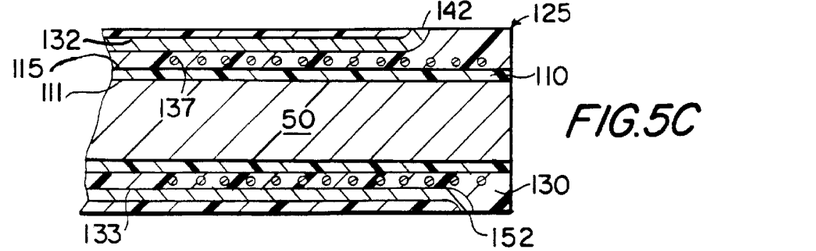
FIG. 5C is a view similar to FIG. 5B showing a still later stage in the FIG. 4 procedure.
Figure 5D:
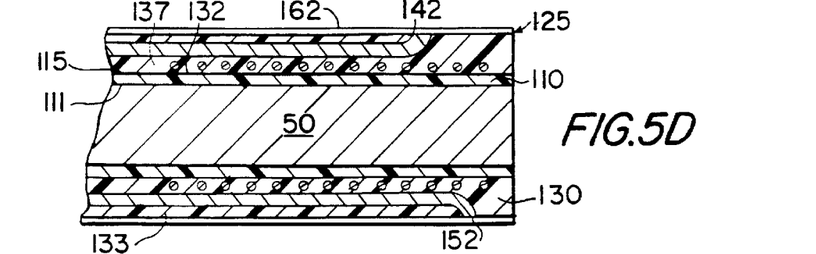
FIG. 5D is a view similar to FIG. 5C showing a even later stage in the FIG. 4 procedure.
Figure 5E:
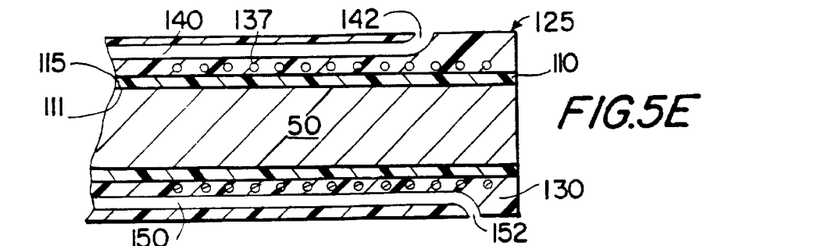
FIG. 5E is a view similar to FIG. 5D showing a further stage in the FIG. 4 procedure.
Figure 5F:
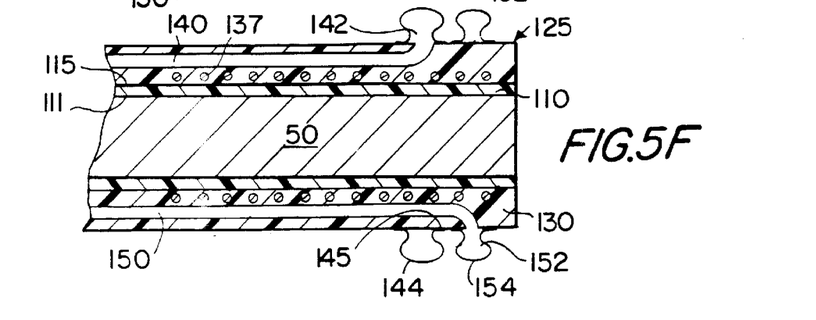
FIG. 5F is a view similar to FIG. 5E showing a last stage before the end result, shown in FIG. 1A, of the procedure depicted by FIG. 4.

In particular, primary mandrel 50 is covered with first layer 110 in step 410 (see FIG. 5A). In step 414, an optional structural layer 137 may be placed over first layer 110 (see FIG. 5B). Then, in step 420, second layer 130 is disposed over outer surface 115 of first layer 110 and optional structural layer 137 (see FIG. 5C). Second layer 130 has at least one secondary mandrel, which is preferably substantially embedded in second layer 130. FIG. 5C shows second layer 130 with embedded secondary mandrels 132 and 133. Next, in step 430, first layer 110 is fused to second layer 130 (FIG. 5D). In step 440, secondary mandrels 132 and 133 are removed from second layer 130 to form secondary lumens 140 and 150, each of which opens through second layer 130 at respective secondary lumen openings 142 and 152 (FIG. 5E). In step 445, balloons 144 and 154 may be formed at respective secondary lumen openings 142 and 152 (FIG. 5F). And, in step 450., primary mandrel 50 is removed from first layer 110 to form primary lumen 120 (e.g., FIG. 1A). As always, the number, positions, and sizes of the integrated secondary mandrels depend on the particular vascular operation being performed.

Also, primary mandrel 50, which forms inner surface 111 of first layer 110, can have any cross sectional shape, but preferably has a generally elliptical shape. Most preferably, it has a circular cross section (e.g., FIG. 1B). These shapes are desirable because they have no sharp corners or edges that may snag or cause friction in primary lumen 120 during operation. Primary mandrel 50 is preferably made of a material capable of withstanding high temperatures and pressures, such as steel, and preferably stainless steel, because fusing step 430 may involve such conditions. Outer diameter 121 of primary mandrel 50 is preferably between about 0.050 inches and about 0.225 inches. For many vascular applications, outer diameter 121 of mandrel 50 (or equivalently inner diameter 121 of first layer 110) can be about 0.160 inches.

First layer 110, which covers primary mandrel 50, may be made from any flexible material, such as many commonly available polymers. Polytetrafluoroethylene is a preferred flexible material. Because one function of first layer 110 is to provide a relatively low friction internal surface 111 for passing devices in primary lumen 120, the outer surface of primary mandrel 50, which may be used to mold inner surface 111, is preferably smooth. Wall thickness 122 of first layer may be between about 0.001 inches and about 0.003 inches. First layer 110 may be deposited onto primary mandrel 50 from a vapor or formed by sliding a first tubular layer over primary mandrel 50.

Unlike inner surface 111, outer surface 115 is preferably rough to facilitate fusion to inner surface 135 of second layer 130. Therefore, outer surface 115 is preferably roughened in step 412 before fusing step 430 so that surfaces 115 and 135 can fuse properly. Roughening may be accomplished by mechanically or chemically etching outer surface 115, such as by treatment with tetrafluoroethylene, or molding or extruding first layer 110 so that outer surface 115 is initially rough.

In step 414, structural layer 137 may be inserted over first layer 110 before disposing step 420, or inserted as an integrated (or embedded) portion of second layer 130 during step 420. If first layer 110 is covered with structural layer 137 in step 414, structural layer 137 should only partially cover first layer 110 so that first layer 110 and second layer 130 are at least partially in contact with each other for fusing in step 430. In this way, structural layer 137 is substantially between first layer 110 and second layer 130. Structural layer 137 may be any material that prevents primary lumen from collapsing, yet provides a flexible skeleton that allows catheter 100 to bend as required, such as stainless steel in the form of a braid or coil, for example.

In step 420, after primary mandrel 50 is covered with first layer 110 (and optionally structural layer 137), second layer 130 is disposed on at least a portion of outer surface 111 of first layer 110. Second layer 130 has at least one secondary mandrel (e.g., mandrels 132 and 133) substantially embedded therein. The secondary mandrels may be placed between first layer 110 and second layer 130 and substantially embedded into second layer 130 during fusing in step 430. Disposing step 420 may include sliding a hollow tube over first layer 110 until the tube substantially covers that layer. The tube, which becomes second layer 130, may be preformed during extrusion or molding so that the tube contains at least one integrated secondary lumen with a removable secondary mandrel. Although a secondary mandrel helps prevent the secondary lumen from collapsing during fusing step 430, in some cases the secondary mandrel may be removed before fusing. The tube that forms second layer 130 may also be preformed with an integrated lumen but without a secondary mandrel. In that case, the secondary mandrel may be embedded into the secondary lumen before fusing step 430.

As described above, secondary lumens 140 and 150 may be integrated anywhere in second layer 130. For example, secondary lumens may be integrated substantially adjacent to inner surface 135 (as shown in FIG. 1B) or outer surface 131 of second layer or tube 130. Secondary lumens 140 and 150 preferably extend longitudinally for at least a portion of catheter 100, but may extend radially (or any direction therebetween) for another portion, as shown near lumen openings 142 and 152. In order to ensure that catheter 100 will not collapse or break during use, minimum thickness 132 of second layer 130 is preferably at least about 0.003 inches along a substantial length of the secondary lumens. Also, as already described above, secondary lumen openings 142 and 152 may be formed at outer surface 131 (FIGS. 1A and 2A), inner surface 135 (FIG. 2C), or distal end 125 of the tube forming second layer 130 (FIG. 2B). As shown in FIGS. 3A and 3B, a single lumen may also have more than one opening.

In fusing step 430, outer surface 115 of first layer 110 is fused to inner surface 135 of second layer 130. As shown in FIG. 5D, this may be accomplished in a series of sub-steps. In one series of sub-steps, heat shrink tubing 162 is placed over second layer 130 in step 431 and heated so that it applies a radially inward force against outer surface 131 of second layer 130 in step 433. The force, in combination with heat, causes first layer 110 to at least partially fuse to second layer 130. Typical fusing temperatures range from about 300° F. to about 600° F. Preferably, the fusing temperature is about 450° F. After heating step 433, heat shrink tubing 162 is preferably removed in step 435.

In an alternate series of sub-steps, fusing may be accomplished by extruding second layer 130 on first layer 110 in step 432 and embedding secondary mandrel 132 and 133 in second layer 130 during extruding in step 434. Then, in step 436, heat is preferably applied to second layer 130 so that first layer 110 fuses to second layer 130. Fusing step 430 may always include applying heat to first layer 110 by heating primary mandrel 50 as well.

In step 445, after fusing in step 430, one or more inflatable balloons 144 and 154 may be formed at integrated secondary lumen openings 142 and 152 by bonding one or more elastic sheets or tubes around those openings. The elastic sheets may be formed from any elastic material, such as polyurethane, silicone, rubber, or latex-based materials and bonded to second layer 130 by applying sufficient heat and/or adhesive (preferred) to a portion of the sheet to cause that portion to partially melt. When the melted portion cools, it forms a fluid, or hemodynamic, seal about the opening so that balloons 144 and 154, which are formed inside the seal, can be inflated and deflated with a fluid, such as a gas or liquid. Alternatively, the elastic sheet may be bonded to a surface of second layer 130 by applying an adhesive material to a portion of the sheet bonded to second layer 130. This works particularly well when the elastic sheet is a silicone, rubber, or latex material. As already described above, the elastic sheet can have any shape, including any preformed shape, as long as it completely covers integrated lumen openings 142 and 152 and has borders 145 and 155 sufficient for bonding.

In steps 440 and 450, the primary and secondary lumens are formed by removing the primary and secondary mandrels, respectively. For example, in step 450, primary lumen 120 is formed by removing primary mandrel 50 from inside first layer 110. Also, in step 440, secondary lumens 140 and 150 are formed by removing secondary mandrels 132 and 133 from second layer 130. Steps 440 and 450 may be performed in any order and before, during, or after balloons 144 and 154 are formed in bonding step 445. However, it is preferable that at least step 445 is performed before step 450 so that primary mandrel 50 provides structural support during step 445.

In step 460, one or more auxiliary apparatus may be inserted in the secondary lumen. Examples of auxiliary apparatus include endoscopic snare instruments (as shown in FIGS. 3A and 3B) and fiber optic bundles. In the case of a snare instrument, inserting step 460 may involve inserting the instrument so that snare loop 354 of instrument 350 is near the secondary lumen opening 356. When snare instrument 350 includes a snare sheath, method 400 may further include inserting the sheath in secondary lumen 340 before or during inserting step 360, in which snare instrument 350 is itself inserted so that the snare loop remains fully open when placed in the primary lumen. The snare loop may be preformed before being inserted. When the auxiliary apparatus includes a fiber optic bundle that has a tip portion, the tip portion may be positioned near a secondary lumen opening (see FIG. 3A).

It will be understood that the foregoing is only illustrative of the principles of the invention, and that various modifications can be made by those skilled in the art without departing from the scope and spirit of the invention. For example, the order of some steps in the procedures that have been described are not critical and can be changed if desired.

The invention claimed is:

1. A catheter having a longitudinal axis and at least one integrated lumen, said catheter comprising:
    a first flexible layer having an outer surface and a primary lumen that extends axially inside said first layer;
    a second flexible layer having an inner surface that is at least partially fused to said outer surface of said first layer, said second layer having at least one secondary lumen that is substantially integrated into said second layer and that opens through said second layer at a secondary lumen opening; and
    an endoscopic snare instrument having a snare loop positioned in said secondary lumen near said secondary lumen opening.

2. The catheter of claim 1 wherein said snare instrument further comprises a snare sheath in which at least a portion of said snare loop is positioned.

3. A catheter having a longitudinal axis, a length, and at least one integrated lumen substantially along said length, said catheter comprising:
    a first flexible layer having an outer surface and a primary lumen that extends axially inside said first layer;
    a second flexible layer having an inner surface that is at least partially fused to said outer surface of said first layer, said second layer having at least one secondary lumen that is substantially integrated into said second layer and that opens through said second layer at a secondary lumen opening; and
    a snare instrument positioned in said secondary lumen and having a snare loop positioned near said secondary lumen opening.

4. The catheter of claim 3 wherein said loop is capable of substantially closing when said loop is inside said at least one secondary lumen.

5. The catheter of claim 3 wherein said loop can open resiliently when extended distally through said secondary lumen opening, said secondary lumen opening being located along said catheter length.

6. The catheter of claim 3 wherein said loop can open resiliently when extended distally through said secondary lumen opening, said secondary lumen opening being at a distal end of said secondary lumen.

7. The catheter of claim 3 wherein said loop can initially be in an open position in said primary lumen for subsequent securing of a device within said primary lumen.

8. The catheter of claim 7 wherein an inner surface of a catheter wall of said primary lumen has a recessed portion for receiving said loop when open so that said loop does not catch on said device when said device is inserted through said primary lumen.

9. The catheter of claim 3 further comprising a device within said primary lumen, and wherein said loop can be retracted into secondary lumen, thereby being able to contract and secure a medical device inside said loop.

10. The catheter of claim 9 wherein, said medical device is selected from a group consisting of a guide wire and a safety wire.

11. The catheter of claim 3 further comprising a medical device positioned at a distal end of said catheter length, wherein said snare can be positioned at said distal end for manipulating said device, said manipulating being selected from a group selected from holding, snaring, and retrieving.

* * * * *